United States Patent [19]
Wozney et al.

[11] Patent Number: 5,849,880
[45] Date of Patent: *Dec. 15, 1998

[54] BONE MORPHOGENETIC PROTEIN (BMP)—6

[75] Inventors: John M. Wozney, Hudson; Elizabeth A. Wang, Carlisle; Vicki A. Rosen, Brookline; Anthony J. Celeste, Hudson, all of Mass.

[73] Assignee: Genetics Institute, Inc., Cambridge, Mass.

[ * ] Notice: The term of this patent shall not extend beyond the expiration date of Pat. No. 5,459,047.

[21] Appl. No.: 469,936

[22] Filed: Jun. 6, 1995

Related U.S. Application Data

[60] Continuation of Ser. No. 251,609, May 27, 1994, Pat. No. 5,459,047, which is a division of Ser. No. 926,081, Aug. 5, 1992, abandoned, which is a division of Ser. No. 490,033, Mar. 7, 1990, Pat. No. 5,187,076, which is a continuation-in-part of Ser. No. 370,544, Jun. 23, 1989, abandoned, which is a continuation-in-part of Ser. No. 347,559, May 4, 1989, abandoned, which is a continuation-in-part of Ser. No. 179,100, Apr. 8, 1988, Pat. No. 5,013,649, Ser. No. 179,101, Apr. 8, 1988, abandoned, and Ser. No. 179,197, Apr. 8, 1988, abandoned, which is a continuation-in-part of Ser. No. 28,285, Mar. 20, 1987, abandoned, and Ser. No. 31,346, Mar. 26, 1987, Pat. No. 4,877,864, which is a continuation-in-part of Ser. No. 943,332, Dec. 17, 1986, abandoned, and Ser. No. 880,776, Jul. 1, 1986, abandoned, said Ser. No. 179,100, and Ser. No. 179,101, each is a continuation-in-part of Ser. No.28,285, and Ser. No. 31,346, said Ser. No. 28,285, is a continuation-in-part of Ser. No. 943,332, and Ser. No. 880,776.

[51] Int. Cl.⁶ .......................... C07K 14/46; A61K 38/18; C07H 21/04; C12P 21/00
[52] U.S. Cl. ..................... 530/399; 530/840; 514/12; 435/69.1; 435/69.4; 435/325; 435/252.3; 536/23.5
[58] Field of Search ................. 435/69.1, 69.4, 435/240.2, 325, 252.3; 424/423, 426; 514/12; 530/399, 840; 536/24.31, 23.51, 23.5

[56] References Cited

U.S. PATENT DOCUMENTS

| | | | |
|---|---|---|---|
| 4,294,753 | 10/1981 | Urist | 530/395 |
| 4,434,094 | 2/1984 | Seyedin et al. | 530/416 |
| 4,455,256 | 6/1984 | Urist | 530/350 |
| 4,563,350 | 1/1986 | Nathan | 424/95 |
| 4,608,199 | 8/1986 | Caplan et al. | 530/414 |
| 4,627,982 | 12/1986 | Seyedin et al. | 424/95 |
| 4,681,763 | 7/1987 | Nathanson | 424/95 |
| 4,737,578 | 4/1988 | Evans | 530/350 |
| 4,761,471 | 8/1988 | Urist | 530/350 |
| 4,774,228 | 9/1988 | Seyedin | 514/21 |
| 4,774,322 | 9/1988 | Seyedin | 530/353 |
| 4,789,732 | 12/1988 | Urist | 530/350 |
| 4,798,885 | 1/1989 | Mason | 530/350 |
| 4,804,744 | 2/1989 | Sen | 530/350 |
| 4,810,691 | 3/1989 | Seyedin | 514/2 |
| 4,843,063 | 6/1989 | Seyedin | 514/2 |
| 4,886,747 | 12/1989 | Derynck . | |
| 4,968,590 | 11/1990 | Kuberasampath et al. | 530/326 |
| 5,011,691 | 4/1991 | Oppermann | 424/423 |
| 5,106,626 | 4/1992 | Parsons et al. . | |
| 5,108,753 | 4/1992 | Kuberasampath . | |
| 5,459,047 | 10/1995 | Wozney et al. | 435/69.1 |

FOREIGN PATENT DOCUMENTS

| | | | |
|---|---|---|---|
| 2 017466 | 5/1990 | Canada | C12N 15/16 |
| 33 6760 | 6/1989 | European Pat. Off. | C07K 7/00 |
| 4 165 78 A2 | 5/1990 | European Pat. Off. | C12N 15/00 |
| 4 094 72 A1 | 11/1990 | European Pat. Off. | C12N 15/12 |
| WO 89/09787 | 10/1989 | WIPO | C07K 13/00 |
| WO 89/09788 | 10/1989 | WIPO | C07K 13/00 |
| WO 90/03733 | 4/1990 | WIPO | A01N 63/02 |
| WO 91/02744 | 3/1991 | WIPO | C07K 15/06 |
| WO 91/05802 | 5/1991 | WIPO | C07K 15/00 |
| WO 91/18047 | 11/1991 | WIPO . | |

OTHER PUBLICATIONS

Urist et al., *Science*, 220: 680–686 (1983).
Luyten et al., *The Journal of Biological Chemistry*, 264(23) 13377–13380 (Aug. 15, 1989).
Sampath, et al., *Proc. Natl Acad. Sci.* 84: 7109–7113 (1987).
Ozkaynak et al., *The EMBO Journal*, v.9 No. 7: 2085–2093 (1990).
Wozney et al., *Science* v. 242, pp. 1528–1534 (1988).
Maniatis et al., Molecular Cloning, a Laboratory Manual Cold Spring Harbor Laboratory CSH N.Y. (1982) p. 310–323 & 404–433.
Lyons et al., *Proc. Natl. Acad Sci* (USA) 86:4554–4558 (Jun. 1989).
Hammonds et al., *Molecular Endocrinology*, 5:149–155 (1991).
Bowie et al. 1990. Deciphering the message in protein sequences: Tolerance to amino acid substitutions. Science, 247:1306–1310. Mar. 1990.
Border et al. 1992. Transforming growth factor–beta in disease: the dark side of tissue repair. J Clin Invest, vol. 90, pp. 1–7. Jul. 1992.

*Primary Examiner*—Elizabeth Kemmerer
*Assistant Examiner*—David S. Romeo
*Attorney, Agent, or Firm*—Ellen j. Kapinos; Steven R. Lazar

[57] ABSTRACT

Purified bone morphogenetic protein (BMP)-6 proteins and processes for producing them are disclosed. The proteins may be used in the treatment of bone and/or cartilage defects and in wound healing and related tissue repair.

15 Claims, 8 Drawing Sheets

FIGURE 1

```
  1  TCTAGAGGTGAGAGCAGCCAACAAGAGAAAAAATCAAAACCGCAATAAATCCGGCTCTCAT   61
     LeuGluValArgAlaAlaAsnLysArgLysAsnGlnAsnArgAsnLysSerGlySerHis
     (1)                                                    (15)

62  CAGGACTCCTCTAGAATGTCCAGTGTTGGAGATTATAACACCAGTGAACAAAAACAAGCC  121
     GlnAspSerSerArgMetSerSerValGlyAspTyrAsnThrSerGluGlnLysGlnAla
             (23)

122  TGTAAAAAGCATGAACTCTATGTGAGTTTCCGGGATCTGGATGGCAGGACTGGATTATA  181
     CysLysLysHisGluLeuTyrValSerPheArgAspLeuGlyTrpGlnAspTrpIleIle
              (42)

182  GCACCAGAAGGATATGCTGCATTTTATTGTGATGGAGAATGTTCTTTTCCACTCAATGCC  241
     AlaProGluGlyTyrAlaAlaPheTyrCysAspGlyGluCysSerPheProLeuAsnAla

242  CATATGAATGCCACCAATCATGCCATAGTTCAGACTCTGGTTCACCTGATGTTTCCTGAC  301
     HisMetAsnAlaThrAsnHisAlaIleValGlnThrLeuValHisLeuMetPheProAsp

302  CACGTACCAAAGCCTTGCTGCGCGACAAACTAAATGCCATCTCTGTGTTGTACTTT  361
     HisValProLysProCysCysAlaThrAsnLysLeuAsnAlaIleSerValLeuTyrPhe

362  GATGACAGCTCCAATGTCATTTTGAAAAAGTACAGAAATATGGTCGTGCGTTCGTGTGGT  421
     AspAspSerSerAsnValIleLeuLeuLysTyrArgAsnMetValValArgSerCysGly

422  TGCCACTAATAGTGCATAATAATGGTAATAAGAAAAAAGATCTGTATGGAGGTTTATGA  481
     CysHisEnd
      (140)

481  CTACAATAAAAAATATCTTTCGGATAAAAGGGGAATTAATAAAATTAGTCTGGCTCATT  540

541  TCATCTCTGTAACCTATGTACAAGAGCATGTATATAGT  578
```

FIGURE 2

```
              9              18             27             36             45
CTG CTG GGC ACG CGT GCT GTG TGG GCC TCA GAG GCG GGC TGG CTG
Leu Leu Gly Thr Arg Ala Val Trp Ala Ser Glu Ala Gly Trp Leu
(1)
             54              63             72             81             90
GAG TTT GAC ATC ACG GCC ACC AGC AAC CTG TGG GTC CTG ACT CCG
Glu Phe Asp Ile Thr Ala Thr Ser Asn Leu Trp Val Leu Thr Pro 99             108            117            126            135
CAG CAC AAC ATG GGG CTG CAG CTG AGC GTG GTC ACG CGT GAT GGG
Gln His Asn MET Gly Leu Gln Leu Ser Val Val Thr Arg Asp Gly 144             153            162            171            180
CTC AGC ATC AGC CCT GGG GCC GCG GGC CTG GTG GGC AGG GAC GGC
Leu Ser Ile Ser Pro Gly Ala Ala Gly Leu Val Gly Arg Asp Gly 189             198            207            216            225
CCC TAC GAC AAG CAG CCC TTC ATG GTG GCC TTC TTC AAG GCC AGT
Pro Tyr Asp Lys Gln Pro Phe MET Val Ala Phe Phe Lys Ala Ser 234             243            252            261            270
GAG GTC CAC GTG CGC AGT GCC CGG TCG GCC CCC GGG CGG CGC CGG
Glu Val His Val Arg Ser Ala Arg Ser Ala Pro Gly Arg Arg Arg 279             288            297            306            315
CAG CAG GCC CGG AAC CGC TCC ACC CCG GCC CAG GAC GTG TCG CGG
Gln Gln Ala Arg Asn Arg Ser Thr Pro Ala Gln Asp Val Ser Arg
                            (97)
            324             333            342            351            360
GCC TCC AGC GCC TCA GAC TAC AAC AGC AGC GAG CTG AAG ACG GCC
Ala Ser Ser Ala Ser Asp Tyr Asn Ser Ser Glu Leu Lys Thr Ala 369             378            387            396            405
TGC CGG AAG CAT GAG CTC TAC GTG AGC TTC CAG GAC CTG GGG TGG
Cys Arg Lys His Glu Leu Tyr Val Ser Phe Gln Asp Leu Gly Trp
(121)       (124)
            414             423            432            441            450
CAG GAC TGG ATC ATT GCC CCC AAG GGC TAC GCT GCC AAC TAC TGT
Gln Asp Trp Ile Ile Ala Pro Lys Gly Tyr Ala Ala Asn Tyr Cys 459             468            477            486            495
GAC GGA GAA TGT TCG TTC CCT CTC AAC GCA CAC ATG AAC GCT ACC
Asp Gly Glu Cys Ser Phe Pro Leu Asn Ala His MET Asn Ala Thr 504             513            522            531            540
AAC CAT GCC ATC GTG CAG ACC CTG GTT CAC CTC ATG AAC CCC GAG
Asn His Ala Ile Val Gln Thr Leu Val His Leu MET Asn Pro Glu 549             558            567            576            585
TAC GTC CCC AAA CCG TGC TGC GCG CCC ACG AAA CTG AAC GCC ATC
Tyr Val Pro Lys Pro Cys Cys Ala Pro Thr Lys Leu Asn Ala Ile 594             603            612            621            630
TCG GTG CTC TAC TTC GAC GAC AAC TCC AAT GTC ATC CTG AAG AAG
Ser Val Leu Tyr Phe Asp Asp Asn Ser Asn Val Ile Leu Lys Lys Tyr Arg Asn
```

FIGURE 2A

```
        639           648          647          666           676
TAC CGG AAC ATG GTC GTA CGA GCG TGT GGG TGC CAC TGACTCGGGG
Tyr Arg Asn MET Val Val Arg Ala Cys Gly Cys His 686           696          706          716           726
TGAGTGGCTG GGGACGCTGT GCACACACTG CCTGGACTCC TGGATCACGT 736           746          756          766           776
CCGCCTTAAG CCCACAGAGG CCCCCGGGAC ACAGGAGGAG ACCCCGAGGC 786           796          806          816           826
CACCTTCGGC TGGCGTTGGC CTTTCCGCCC AACGCAGACC CGAAGGGACC 836           846          856          866           876
CTGTCCGCCC CTTGCTCACA CCGTGAGCGT TGTGAGTAGC CATCGGCTC

886
TAGGAAGCAG CACTCGAG
```

FIGURE 3

```
           10         20         30         40         50
CGACCATGAG AGATAAGGAC TGAGGGCCAG GAAGGGGAAG CGAGCCCGCC 60         70         80         90        100
GAGAGGTGGC GGGGACTGCT CACGCCAAGG GCCACAGCGG CCGCGCTCCG 110        120        130        140        150
GCCTCGCTCC GCCGCTCCAC GCCTCGCGGG ATCCGCGGGG GCAGCCCGGC 159        168        177        186        195
CGGGCGGGG ATG CCG GGG CTG GGG CGG AGG GCG CAG TGG CTG TGC
           MET Pro Gly Leu Gly Arg Arg Ala Gln Trp Leu Cys
           (1)

204        213        222        231        240
TGG TGG TGG GGG CTG CTG TGC AGC TGC TGC GGG CCC CCG CCG CTG
Trp Trp Trp Gly Leu Leu Cys Ser Cys Cys Gly Pro Pro Pro Leu 249        258        267        276        285
CGG CCG CCC TTG CCC GCT GCC GCG GCC GCC GCC GCC GGG GGG CAG
Arg Pro Pro Leu Pro Ala Ala Ala Ala Ala Ala Ala Gly Gly Gln 294        303        312        321        330
CTG CTG GGG GAC GGC GGG AGC CCC GGC CGC ACG GAG CAG CCG CCG
Leu Leu Gly Asp Gly Gly Ser Pro Gly Arg Thr Glu Gln Pro Pro 339        348        357        366        375
CCG TCG CCG CAG TCC TCC TCG GGC TTC CTG TAC CGG CGG CTC AAG
Pro Ser Pro Gln Ser Ser Ser Gly Phe Leu Tyr Arg Arg Leu Lys 384        393        402        411        420
ACG CAG GAG AAG CGG GAG ATG CAG AAG GAG ATC TTG TCG GTG CTG
Thr Gln Glu Lys Arg Glu MET Gln Lys Glu Ile Leu Ser Val Leu 429        438        447        456        465
GGG CTC CCG CAC CGG CCC CGG CCC CTG CAC GGC CTC CAA CAG CCG
Gly Leu Pro His Arg Pro Arg Pro Leu His Gly Leu Gln Gln Pro 474        483        492        501        510
CAG CCC CCG GCG CTC CGG CAG CAG GAG GAG CAG CAG CAG CAG CAG
Gln Pro Pro Ala Leu Arg Gln Gln Glu Glu Gln Gln Gln Gln Gln 519        528        537        546        555
CAG CTG CCT CGC GGA GAG CCC CCT CCC GGG CGA CTG AAG TCC GCG
Gln Leu Pro Arg Gly Glu Pro Pro Pro Gly Arg Leu Lys Ser Ala 564        573        582        591        600
CCC CTC TTC ATG CTG GAT CTG TAC AAC GCC CTG TCC GCC GAC AAC
Pro Leu Phe MET Leu Asp Leu Tyr Asn Ala Leu Ser Ala Asp Asn 609        618        627        636        645
GAC GAG GAC GGG GCG TCG GAG GGG GAG AGG CAG CAG TCC TGG CCC
Asp Glu Asp Gly Ala Ser Glu Gly Glu Arg Gln Gln Ser Trp Pro
```

FIGURE 3A

```
              654              663              672              681              690
     CAC GAA GCA GCC AGC TCG TCC CAG CGT CGG CAG CCG CCC CCG GGC
     His Glu Ala Ala Ser Ser Ser Gln Arg Arg Gln Pro Pro Pro Gly Ser 699              708              717              726              735
     GCC GCG CAC CCG CTC AAC CGC AAG AGC CTT CTG GCC CCC GGA TCT
     Pro Pro Gly Ala Ala His Pro Leu Asn Arg Lys Ser Leu Leu Ala 744              753              762              771              780
     GGC AGC GGC GGC GCG TCC CCA CTG ACC AGC GCG CAG GAC AGC GCC
     Gly Ser Gly Gly Ala Ser Pro Leu Thr Ser Ala Gln Asp Ser Ala
              789              798              807              816              825
     TTC CTC AAC GAC GCG GAC ATG GTC ATG AGC TTT GTG AAC CTG GTG
     Phe Leu Asn Asp Ala Asp MET Val MET Ser Phe Val Asn Leu Val 834              843              852              861              870
     GAG TAC GAC AAG GAG TTC TCC CCT CGT CAG CGA CAC CAC AAA GAG
     Glu Tyr Asp Lys Glu Phe Ser Pro Arg Gln Arg His His Lys Glu 879              888              897              906              915
     TTC AAG TTC AAC TTA TCC CAG ATT CCT GAG GGT GAG GTG GTG ACG
     Phe Lys Phe Asn Leu Ser Gln Ile Pro Glu Gly Glu Val Val Thr 924              933              942              951              960
     GCT GCA GAA TTC CGC ATC TAC AAG GAC TGT GTT ATG GGG AGT TTT
     Phe Arg Ile Tyr Lys Asp Cys Val MET Ala Ala Glu Gly Ser Phe 969              978              987              996             1005
     AAA AAC CAA ACT TTT CTT ATC AGC ATT TAT CAA GTC TTA CAG GAG
     Lys Asn Gln Thr Phe Leu Ile Ser Ile Tyr Gln Val Leu Gln Glu 1014             1023             1032             1041             1050
     CAT CAG CAC AGA GAC TCT GAC CTG TTT TTG TTG GAC ACC CGT GTA
     His Gln His Arg Asp Ser Asp Leu Phe Leu Leu Asp Thr Arg Val
             1059             1068             1077             1086             1095
     GTA TGG GCC TCA GAA GAA GGC TGG CTG GAA TTT GAC ATC ACG GCC
     Val Trp Ala Ser Glu Glu Gly Trp Leu Glu Phe Asp Ile Thr Ala 1104             1113             1122             1131             1140
     ACT AGC AAT CTG TGG GTT GTG ACT CCA CAG CAT AAC ATG GGG CTT
     Thr Ser Asn Leu Trp Val Val Thr Pro Gln His Asn MET Gly Leu 1149             1158             1167             1176             1185
     CAG CTG AGC GTG GTG ACA AGG GAT GGA GTC CAC GTC CAC CCC CGA
     Gln Leu Ser Val Val Thr Arg Asp Gly Val His Val His Pro Arg 1194             1203             1212             1221             1230
     GCC GCA GGC CTG GTG GGC AGA GAC GGC CCT TAC GAT AAG CAG CCC
     Ala Ala Gly Leu Val Gly Arg Asp Gly Pro Tyr Asp Lys Gln Pro 1239             1248             1257             1266             1275
     TTC ATG GTG GCT TTC TTC AAA GTG AGT GAG GTC CAC GTG CGC ACC
     Phe MET Val Ala Phe Phe Lys Val Ser Glu Val His Val Arg Thr
```

FIGURE 3B

```
         1284        1293        1302        1311        1320
ACC AGG TCA GCC TCC AGC CGG CGC CGA CAA CAG AGT CGT AAT CGC
Thr Arg Ser Ala Ser Ser Arg Arg Arg Gln Gln Ser Arg Asn Arg
                                    (382)
         1329        1338        1347        1356        1365
TCT ACC CAG TCC CAG GAC GTG GCG CGG GTC TCC AGT GCT TCA GAT
Ser Thr Gln Ser Gln Asp Val Ala Arg Val Ser Ser Ala Ser Asp
(388)

1374        1383        1392        1401        1410
TAC AAC AGC AGT GAA TTG AAA ACA GCC TGC AGG AAG CAT GAG CTG
Tyr Asn Ser Ser Glu Leu Lys Thr Ala Cys Arg Lys His Glu Leu
                                                (412)
         1419        1428        1437        1446        1455
TAT GTG AGT TTC CAA GAC CTG GGA TGG CAG GAC TGG ATC ATT GCA
Tyr Val Ser Phe Gln Asp Leu Gly Trp Gln Asp Trp Ile Ile Ala 1464        1473        1482        1491        1500
CCC AAG GGC TAT GCT GCC AAT TAC TGT GAT GGA GAA TGC TCC TTC
Pro Lys Gly Tyr Ala Ala Asn Tyr Cys Asp Gly Glu Cys Ser Phe 1509        1518        1527        1536        1545
CCA CTC AAC GCA CAC ATG AAT GCA ACC AAC CAC GCG ATT GTG CAG
Pro Leu Asn Ala His MET Asn Ala Thr Asn His Ala Ile Val Gln 1554        1563        1572        1581        1590
ACC TTG GTT CAC CTT ATG AAC CCC GAG TAT GTC CCC AAA CCG TGC
Thr Leu Val His Leu MET Asn Pro Glu Tyr Val Pro Lys Pro Cys 1599        1608        1617        1626        1635
TGT GCG CCA ACT AAG CTA AAT GCC ATC TCG GTT CTT TAC TTT GAT
Cys Ala Pro Thr Lys Leu Asn Ala Ile Ser Val Leu Tyr Phe Asp 1644        1653        1662        1671        1680
GAC AAC TCC AAT GTC ATT CTG AAA AAA TAC AGG AAT ATG GTT GTA
Asp Asn Ser Asn Val Ile Leu Lys Lys Tyr Arg Asn MET Val Val 1689        1698        1708        1718        1728
AGA GCT TGT GGA TGC CAC TAACTCGAAA CCAGATGCTG GGGACACACA
Arg Ala Cys Gly Cys His
                     (513)

1738       1748       1758       1768       1778
TTCTGCCTTG GATTCCTAGA TTACATCTGC CTTAAAAAAA CACGGAAGCA 1788       1798       1808       1818       1828
CAGTTGGAGG TGGGACGATG AGACTTTGAA ACTATCTCAT GCCAGTGCCT 1838       1848       1858       1868       1878
TATTACCCAG GAAGATTTTA AAGGACCTCA TTAATAATTT GCTCACTTGG 1888       1898       1908       1918       1928
TAAATGACGT GAGTAGTTGT TGGTCTGTAG CAAGCTGAGT TTGGATGTCT
```

FIGURE 3C

```
           1938       1948       1958       1968       1978
       GTAGCATAAG GTCTGGTAAC TGCAGAAACA TAACCGTGAA GCTCTTCCTA 1988       1998       2008       2018       2028
       CCCTCCTCCC CCAAAAACCC ACCAAAATTA GTTTTAGCTG TAGATCAAGC 2038       2048       2058       2068       2078
       TATTTGGGGT GTTTGTTAGT AAATAGGGAA AATAATCTCA AAGGAGTTAA 2088       2098       2108       2118       2128
       ATGTATTCTT GGCTAAAGGA TCAGCTGGTT CAGTACTGTC TATCAAAGGT 2138       2148       2158       2168       2178
       AGATTTTACA GAGAACAGAA ATCGGGGAAG TGGGGGGAAC GCCTCTGTTC 2188       2198       2208       2218       2228
       AGTTCATTCC CAGAAGTCCA CAGGACGCAC AGCCCAGGCC ACAGCCAGGG 2238       2248       2258       2268       2278
       CTCCACGGGG CGCCCTTGTC TCAGTCATTG CTGTTGTATG TTCGTGCTGG 2288       2298       2308       2318       2328
       AGTTTTGTTG GTGTGAAAAT ACACTTATTT CAGCCAAAAC ATACCATTTC 2338       2348       2358       2368       2378
       TACACCTCAA TCCTCCATTT GCTGTACTCT TTGCTAGTAC CAAAAGTAGA 2388       2398       2408       2418       2428
       CTGATTACAC TGAGGTGAGG CTACAAGGGG TGTGTAACCG TGTAACACGT 2438       2448       2458       2468       2478
       GAAGGCAGTG CTCACCTCTT CTTTACCAGA ACGGTTCTTT GACCAGCACA 2488       2498       2508       2518       2528
       TTAACTTCTG GACTGCCGGC TCTAGTACCT TTTCAGTAAA GTGGTTCTCT 2538       2548       2558       2568       2578
       GCCTTTTTAC TATACAGCAT ACCACGCCAC AGGGTTAGAA CCAACGAAGA 2588       2598       2608       2618       2628
       AAATAAAATG AGGGTGCCCA GCTTATAAGA ATGGTGTTAG GGGGATGAGC 2638       2648       2658       2668       2678
       ATGCTGTTTA TGAACGGAAA TCATGATTTC CCTGTAGAAA GTGAGGCTCA 2688       2698       2708       2718       2728
       GATTAAATTT TAGAATATTT TCTAAATGTC TTTTTCACAA TCATGTGACT 2738       2748       2758       2768       2778
       GGGAAGGCAA TTTCATACTA AACTGATTAA ATAATACATT TATAATCTAC 2788       2798       2808       2818       2828
       AACTGTTTGC ACTTACAGCT TTTTTTGTAA ATATAAACTA TAATTTATTG
```

FIGURE 3D

```
        2838       2848       2858       2868       2878
   TCTATTTTAT ATCTGTTTTG CTGTGGCGTT GGGGGGGGGG CCGGGCTTTT 2888       2898       2908       2918
   GGGGGGGGGG GTTTGTTTGG GGGGTGTCGT GGTGTGGGCG GGCGG
```

BONE MORPHOGENETIC PROTEIN (BMP) — 6

CROSS REFERENCES TO RELATED APPLICATIONS

This application is a continuation of U.S. Ser. No. 08/251,069 now U.S. Pat. No. 5,459,047 filed May 27, 1994, which is a divisional of U.S. Ser. No. 07/926,081 filed Aug. 5, 1992, now abandoned, which is a divisional of U.S. Ser. No. 07/490,033 now U.S. Pat. No. 5,187,076 filed Mar. 7, 1990, which is a continuation-in-part of U.S. Ser. No. 07/370,544 filed Jun. 23, 1989, now abandoned, which is a continuation-in-part of U.S. Ser. No. 07/347,559 filed May 4, 1989 (now abandoned), which is a continuation-in-part of U.S. Ser. Nos. 07/179,100 now U.S. Pat. No. 5,013,649; 07/179,101 (now abandoned); and 07/179,197 filed Apr. 8, 1988, now abandoned, which are continuations-in-part of U.S. Ser. Nos. 07/028,285 filed Mar. 20, 1987 (now abandoned); and 07/031,346 now U.S. Pat. No. 4,877,864 filed Mar. 26, 1987, now U.S. Pat. No. 4,877,864, which are continuations-in-part of U.S. Ser. Nos. 06/943,332 filed Dec. 17, 1986 (now abandoned;) and 06/880,776 filed Jul. 1, 1986 (now abandoned).

The present invention relates to a family of purified proteins, termed BMP-6 proteins (wherein BMP is bone morphogenic protein), which exhibit the ability to induce cartilage and/or bone formation and processes for obtaining them. These proteins may be used to induce bone and/or cartilage formation and in wound healing and tissue repair.

The invention provides purified human BMP-6 proteins, substantially free from other proteins with which they are co-produced. The BMP-6 proteins of the invention are characterized by an amino acid sequence comprising acid #412 to amino acid #513 set forth in FIG. 3. The amino acid sequence from amino acid #412 to #513 is encoded by the DNA sequence of FIG. 3 from nucleotide #1393 to nucleotide #1698. These proteins may be further characterized by an apparent molecular weight of 28,000–30,000 daltons as determined by sodium dodecyl sulfate polyacrylamide gel electrophoresis (SDS-PAGE). Under reducing conditions in SDS-PAGE the protein electrophoreses with a molecular weight of approximately 14,000–20,000 daltons. It is contemplated that these proteins are capable of stimulating promoting, or otherwise inducing cartilage and/or bone formation.

The invention, further provides bovine BMP-6 proteins characterized by the amino acid sequence comprising amino acid #121 to amino acid #222 set forth in FIG. 2. The amino acid sequence from #121 to #222 is encoded by the DNA sequence of FIG. 2 from nucleotide #361 to #666 of FIG. 2. These proteins may be further characterized by an apparent molecular weight of 28,000–30,000 daltons as determined by sodium dodecyl sulfate polyacrylamide gel electrophoresis (SDS-PAGE). Under reducing conditions in SDS-PAGE the protein electrophoreses with a molecular weight of approximately 14,000–20,000 daltons. It is contemplated that these proteins are capable of inducing cartilage and/or bone formation.

Human BMP-6 proteins of the invention are produced by culturing a cell transformed with a DNA sequence comprising nucleotide #1393 to nucleotide #1698 as shown in FIG. 3 or a substantially similar sequence, recovering and purifying from the culture medium a protein comprising amino acid #412 to amino acid #513 or a substantially similar sequence.

Bovine proteins of the invention may be produced by culturing a cell transformed with a DNA comprising nucleotide #361 through nucleotide #666 as set forth in FIG. 2 or a substantially similar sequence and recovering and purifying from the culture medium a protein comprising amino acid #121 to amino acid #222 as set forth in FIG. 2.

The invention further provides a method wherein the proteins described above are utilized for obtaining related human protein/s or other mammalian cartilage and/or bone formation protein/s. Such methods are known to those skilled in the art of genetic engineering. One method for obtaining such proteins involves utilizing the human BMP-6 coding sequence or a portion thereof from nucleotide #160–#1698 to design probes for screening human genomic and/or cDNA libraries to isolate human genomic and/or cDNA sequences. Additional methods within the art may employ the bovine and human BMP-6 proteins of the invention to obtain other mammalian BMP-6 cartilage and/or bone formation proteins. Having identified the nucleotide sequences, the proteins are produced by culturing a cell transformed with the nucleotide sequence. This sequence or portions thereof hybridizes under stringent conditions to the nucleotide sequence substantially as shown in Table II comprising nucleotide #1 to nucleotide #666 or the nucleotide sequence or portions thereof substantially as shown in FIG. 3 comprising nucleotide #160 to #1698 and encodes a protein exhibiting cartilage and/or bone formation activity. The expressed protein is recovered and purified from the culture medium. The purified BMP-6 proteins of the invention are substantially free from other proteinaceous materials with which they are coproduced, as well as from other contaminants.

The BMP-6 proteins of the invention are further characterized by the ability to promote, stimulate or otherwise induce the formation of cartilage and/or bone. It is further contemplated that the ability of these proteins to induce the formation of cartilage and/or bone is exhibited by the ability to demonstrate cartilage and/or bone formation activity in the rat bone formation assay described below. It is further contemplated that the proteins of then demonstrate activity in this rat bone assay at a concentration of 10 $\mu$g–500 $\mu$g/gram of bone formed. More particularly, it is contemplated these proteins may be characterized by the ability of 1 $\mu$g of the protein to score at least +2 in the rat bone formation assay described below using either the original or modified scoring method.

Another aspect of the invention provides pharmaceutical compositions containing a therapeutically effective amount of a protein of the invention in a pharmaceutically acceptable vehicle or carrier. These compositions of the invention may be used to induce bone and/or cartilage formation. These compositions may also be used for wound healing and tissue repair. Further compositions of the invention may include, in addition to a BMP-6 protein, at least one other therapeutically useful agent such as the proteins designated BMP-1, BMP-2A and -2B, BMP-3, BMP-5, and BMP-7 disclosed respectively in co-owned U.S. Pat. No. 5,013,649, Ser. No. 179,101, abandoned, and Ser. No. 179,197, abandoned U.S. Pat. No. 5,141,905, Ser. No. 438,919, now U.S. Pat. No. 5,141,905. Other therapeutically useful agents include growth factors such as epidermal growth factor (EGF), fibroblast growth factor (FGF), transforming growth factors (TGF-$\alpha$ and TGF-$\beta$) and platelet derived growth factor (PDGF). The compositions of the invention may also include an appropriate matrix, for instance, for delivery and support of the composition and/or providing a surface for bone and/or cartilage growth.

The compositions may be employed in methods for treating a number of bone and/or cartilage defects, and periodontal disease. They may also be employed in methods for treating various types of wounds and in tissue repair. These methods, according to the invention, entail administering to a patient needing such bone and/or cartilage formation, wound healing or tissue repair, a therapeutically effective amount of a BMP-6 protein of the invention in a pharmaceutically acceptable vehicle or carrier including a martrix. These methods may also entail the administration of a BMP-6 protein in conjunction with at least one of the "BMP" proteins disclosed in the co-owned applications described above. In addition, these methods may also include the administration of a protein of the invention with other growth factors including EGF, FGF, TGF-α, TGF-β, and PDFG.

Still a further aspect of the invention are DNA sequences coding for expression of a protein of the invention. Such sequences include the sequence of nucleotides in a 5' to 3' direction illustrated in FIG. 2 or FIG. 3 or DNA sequences which hybridize under stringent conditions with the DNA sequence of FIG. 2 or FIG. III and encode a protein demonstrating ability to induce cartilage and/or bone formation. Such ability to induce cartilage and/or bone formation may be demonstrated in the rat bone formation assay described below. It is contemplated that these proteins demonstrate activity in this assay at a concentration of 10 μg–500 μg/gram of bone formed. More particularly, it is contemplated that these proteins demonstrate the ability of 1 μg of the protein to score at least +2 in the rat bone formation assay using either the original or modified scoring method. Allelic or variations as described herein below of the sequences of FIG. 2 and 3, whether such nucleotide changes result in changes in the peptide sequence or not, are also included in the present invention.

A further aspect of the invention provides vectors containing a DNA sequence as described above in operative association with an expression control sequence therefor. These vectors may be employed in a novel process for producing a protein of the invention in which a cell line transformed with a DNA sequence directing expression of a protein of the invention in operative association with an expression control sequence therefor, is cultured in a suitable culture medium and a protein of the invention is isolated and purified therefrom. This claimed process may employ a number of known cells, both prokaryotic and eukaryotic, as host cells for expression of the polypeptide.

Other aspects and advantages of the present invention will be apparent upon consideration of the following detailed description and preferred embodiments thereof.

BRIEF DESCRIPTION OF THE DRAWING

FIG. 1 comprises DNA sequence and derived amino acid sequence of bovine BMP-5.

FIG. 2 comprises DNA sequence and derived amino acid sequence of bovine BMP-6.

FIG. 3 comprises DNA sequence and derived amino acid sequence of human BMP-6 from BMP6C35 ATCC #68245.

DETAILED DESCRIPTION OF THE INVENTION

The purified human BMP-6 proteins of the invention are characterized by an amino acid sequence comprising amino acid #412 to #513 as set forth in FIG. 3. In one embodiment a BMP-6 protein of the invention comprises amino acid #388 to #513 of FIG. 3. In a further embodiment the BMP-6 protein comprises amino acid #382 to #513 of FIG. 3.

The purified BMP-6 human cartilage/bone proteins of the present invention may be produced by culturing a host cell transformed with a DNA sequence comprising nucleotide #1393 to nucleotide #1698 as set forth in FIG. 3 or substantially homologous sequences operatively linked to a heterologous regulatory control sequence and recovering, isolating and purifying from the culture medium a protein comprising amino acid #412 to amino acid #513 as set forth in FIG. 3 or a substantially homologous sequence.

In another embodiment, purified human BMP-6 proteins may be produced by culturing a host cell transformed with a DNA sequence comprising nucleotide #1321 to #1698 as set forth in FIG. 3 or substantially homologous sequences operatively linked to a heterologous regulatory control sequence and recovering and purifying from the culture medium a protein comprising amino acid #388 to #513 asset forth in FIG. 3 or a substantially homologous sequence.

In another embodiment, purified human BMP-6 proteins may be produced by culturing a host cell transformed with a DNA sequence comprising nucleotide #1303 to #1698 as set forth in FIG. 3 or substantially homologous sequences operatively linked to a heterologous regulatory control sequence and recovering and purifying from the culture medium a protein comprising amino acid #382 to #513 as set forth in FIG. 3 or a substantially homologous sequence.

The purified human BMP-6 proteins are substantially free from other proteinaceous materials with which they are co-produced, as well as from other contaminants.

Purified BMP-6 bovine cartilage/bone protein of the present invention are produced by culturing a host cell transformed with a DNA sequence comprising nucleotide #361 to nucleotide #666 as set forth in FIG. 2 or substantially homologous sequences and recovering from the culture medium a protein comprising amino acid #121 to amino acid #222 as set forth in FIG. 2 or a substantially homologous sequence. In another embodiment the bovine protein is produced by culturing a host cell transformed with a sequence comprising nucleotide #289 to #666 of FIG. 2 and recovering and purifying a protein comprising amino acid #97 to amino acid #222. The purified BMP-6 bovine proteins are substantially free from other proteinaceous materials with which they are co-produced, as well as from other contaminants.

These proteins of the invention may be further characterized by the ability to demonstrate cartilage and/or bone formation activity. This activity may be demonstrated, for example, in the rat bone formation assay as described in Example III. It is further contemplated that these proteins demonstrate activity in the assay at a concentration of 10 μg–500 μg/gram of bone formed. The proteins may be further characterized by the ability of 1 μg to score at least +2 in this assay.

BMP-6 proteins may be further characterized by an apparent molecular weight of 28,000–30,000 daltons as determined by sodium dodecyl sulfate polyacrylamide gel electrophoresis (SDS-PAGE). Under reducing conditions in SDS-PAGE, the protein electrophoreses with a molecular weight of approximately 14,000–20,000 daltons.

The proteins provided herein also include factors encoded by the sequences similar to those of FIG. 2 and FIG. 3 but into which modifications are naturally provided (e.g. allelic variations in the nucleotide sequence which may result in amino acid changes in the polypeptide) or deliberately engineered. Similarly, synthetic polypeptides which wholly or partially duplicate continuous sequences of the amino acid residues of FIG. 2 or FIG. 3 are encompassed by the invention. These sequences, by virtue of sharing primary, secondary, or tertiary structural and conformational characteristics with other cartilage/bone proteins of the invention may possess bone and/or cartilage growth factor biological properties in common therewith. Thus, they may be employed as biologically active substitutes for naturally-occurring proteins in therapeutic processes.

Other specific mutations of the sequences of the proteins of the invention described herein may involve modifications of a glycosylation site. These modifications may involve O-linked or N-linked glycosylation sites. For instance, the absence of glycosylation or only partial glycosylation at the asparagine-linked glycosylation sites results from amino acid substitution or deletion at the asparagine-linked glycosylation recognition sites present in the sequences of the proteins of the invention, for example, as shown in FIG. 2 or FIG. 3. The asparagine-linked glycosylation recognition sites comprise tripeptide sequences which are specifically recognized by appropriate cellular glycosylation enzymes. These tripeptide sequences are either asparagine-X-threonine or asparagine-X-serine, where X is usually any amino acid. A variety of amino acid substitutions or deletions at one or both of the first or third amino acid positions of a glycosylation recognition site (and/or amino acid deletion at the second position) results in non-glycosylation at the modified tripeptide sequence. Expression of such altered nucleotide sequences produces variants which are not glycosylated at that site.

The present invention also encompasses the novel DNA sequences, free of association with DNA sequences encoding other proteinaceous materials, and coding on expression for the proteins of the invention. These DNA sequences include those depicted in FIGS. 2 and 3 in a 5' to 3' direction or portions thereof. Further included are those sequences which hybridize under stringent hybridization conditions [see, T. Maniatis et al, *Molecular Cloning (A Laboratory Manual)*, Cold Spring Harbor Laboratory (1982), pages 387 to 389] to the DNA sequence of FIG. 2 or FIG. 3 and demonstrate cartilage and/or bone formation activity. Such cartilage and/or bone formation activity may be in the rat bone formation assay. An example of one such stringent hybridization condition is hybridization at 4× SSC at 65° C., followed by a washing in 0.1× SCC at 65° C. for an hour. Alternatively, an exemplary stringent hybridization condition is in 50% formamide, 4× SCC at 42° C.

Similarly, DNA sequences which encode proteins similar to the protein encoded by the sequence of FIG. 2 or FIG. 3, but which differ in codon sequence due to the degeneracies of the genetic code or allelic variations (naturally-occurring base changes in the species population which may or may not result in an amino acid change) also encode the proteins of the invention described herein. Variations in the DNA sequences of FIG. 2 and FIG. 3 which are caused by point mutations or by induced modifications (including insertion, deletion, and substitution) to enhance the activity, half-life or production of the polypeptides encoded thereby are also encompassed in the invention.

In a further aspect, the invention provides a method for obtaining related human proteins or other mammalian BMP-6 proteins. One method for obtaining such proteins entails, for instance, utilizing the human BMP-6 coding sequence disclosed herein to probe a human genomic library using standard techniques for the human gene or fragments thereof. Sequences thus identified may also be used as probes to identify a human cell line or tissue which synthesizes the analogous cartilage/bone protein. A cDNA library is synthesized and screened with probes derived from the human or bovine coding sequences. The human sequence thus identified is transformed into a host cell, the host cell is cultured and the protein recovered, isolated and purified from the culture medium. The purified protein is predicted to exhibit cartilage and/or bone formation activity. This activity may be demonstrated in the rat bone formation assay of Example III.

Another aspect of the present invention provides a novel method for producing the proteins of the invention. This method involves culturing a suitable cell line, which has been transformed with a DNA sequence coding for expression of a protein of the invention, under the control of known regulatory sequences. Regulatory sequences include promoter fragments, terminator fragments and other suitable sequences which direct the expression of the protein in an appropriate host cell. Methods for culturing suitable cell lines are within the skill of the art. The transformed cells are cultured and the BMP-6 proteins expressed thereby are recovered and purified from the culture medium using purification techniques known to those skilled in the art. The purified BMP-6 proteins are substantially free from other proteinaceous materials with which they are co-produced, as well as other contaminants. Purified BMP-6 proteins of the invention are substantially free from materials with which the proteins of the invention exist in nature.

Suitable cells or cell lines may be mammalian cells, such as Chinese hamster ovary cells (CHO). The selection of suitable mammalian host cells and methods for transformation, culture, amplification, screening and product production and purification are known in the art. See, e.g., Gething and Sambrook, *Nature*, 293:620–625 (1981), or alternatively, Kaufman et al, *Mol. Cell. Biol.*, 5(7) :1750–1759 (1985) or Howley et al, U.S. Pat. No. 4,419,446. Other suitable mammalian cell lines are the monkey COS-1 cell line and the CV-1 cell line.

Bacterial cells may also be suitable hosts. For example, the various strains of *E. coli* (e.g., HB101, MC1061) are well-known as host cells in the field of biotechnology. Various strains of *B. subtilis*, Pseudomonas, other bacilli and the like may also be employed in this method.

Many strains of yeast cells known to those skilled in the art may also be available as host cells for expression of the polypeptides of the present invention. Additionally, where desired, insect cells may be utilized as host cells in the method of the present invention. See, e.g. Miller et al, *Genetic Engineering*, 8:277–298 (Plenum Press 1986) and references cited therein.

Another aspect of the present invention provides vectors for use in the method of expression of the proteins of the invention. Preferably the vectors contain the full novel DNA sequences described above which code for the novel BMP-6 proteins of the invention. Additionally the vectors also contain appropriate expression control sequences permitting expression of the protein sequences. Alternatively, vectors incorporating modified sequences as described above are also embodiments of the present invention and useful in the production of the proteins of the invention. The vectors may be employed in the method of transforming cell lines and contain selected regulatory sequences in operative association with the DNA coding sequences of the invention which are capable of directing the replication and expression thereof in selected host cells. Useful regulatory sequences for such vectors are known to those skilled in the art and may be selected depending upon the selected host cells. Such selection is routine and does not form part of the present invention. Host cells transformed with such vectors and progeny thereof for use in producing BMP-6 proteins are also provided by the invention.

A protein of the present invention, which induces cartilage and/or bone formation in circumstances where bone and/or cartilage is not normally formed, has application in the healing of bone fractures and cartilage defects in humans and other animals. Such a preparation employing a protein of the invention may have prophylactic use in closed as well as open fracture reduction and also in the improved fixation of artificial joints. De novo bone formation induced by an osteogenic agent contributes to the repair of congenital, trauma induced, or oncologic resection induced craniofacial defects, and also is useful in cosmetic plastic surgery. A protein of the invention may be used in the treatment of periodontal disease, and in other tooth repair processes. Such agents may provide an environment to attract bone-forming cells, stimulate growth of bone-forming cells or induce differentiation of progenitors of bone-forming cells. A variety of osteogenic, cartilage-inducing and bone inducing factors have been described. See, e.g. European patents 148,155 and 169,016 for discussions thereof.

The proteins of the invention may also be used in wound healing and related tissue repair. The types of wounds include, but are not limited to burns, incisions and ulcers. (See, e.g. PCT Publication WO84/01106 for discussion of wound healing and related tissue repair).

A further aspect of the invention is a therapeutic method and composition for repairing fractures and other conditions related to bone and/or cartilage defects or periodontal diseases. In addition, the invention comprises therapeutic methods and compositions for wound healing and tissue repair. Such compositions comprise a therapeutically effective amount of at least one of the BMP-6 proteins of the invention in admixture with a pharmaceutically acceptable vehicle, carrier or matrix.

It is expected that the proteins of the invention may act in concert with or perhaps synergistically with one another or with other related proteins and growth factors. Therapeutic methods and compositions of the invention therefore comprise one or more of the proteins of the present invention. Further therapeutic methods and compositions of the invention therefore comprise a therapeutic amount of at least one protein of the invention with a therapeutic amount of at least one of the other "BMP" proteins, BMP-1, BMP-2 (BMP-2A, BMP-2 Class I), BMP-3, BMP-4 (BMP-2B, BMP-2 Class II), BMP-5 and BMP-7, disclosed in co-owned and co-pending U.S. applications described above. Such methods and compositions of the invention may comprise proteins of the invention or portions thereof in combination with the above-mentioned "BMP" proteins or portions thereof. Such combination may comprise individual separate molecules from each of the proteins or heteromolecules such as heterodimers formed by portions of the respective proteins. For example, a method and composition of the invention may comprise a BMP-6 protein of the invention or a portion thereof linked with a portion of a different "BMP" protein to form a heteromolecule.

Further therapeutic methods and compositions of the invention comprise the proteins of the invention or portions thereof in combination with other agents beneficial to the treatment of the bone and/or cartilage defect, wound, or tissue in question. These agents include various growth factors such as epidermal growth factor (EGF), fibroblast growth factor (FGF), platelet derived growth factor (PDGF), transforming growth factors (TGF-α and TGF-β), k-fibroblast growth factor (kFGF), parathyroid hormone (PTH), leukemia inhibitory factor (LIF/HILDA/DIA), and insulin-like growth factors (IGF-I and IGF-II). Portions of these agents may also be used in compositions of the invention.

The preparation and formulation of such physiologically acceptable protein compositions, having due regard to pH, isotonicity, stability and the like, is within the skill of the art. The therapeutic compositions are also presently valuable for veterinary applications due to the apparent lack of species specificity in cartilage and bone proteins. Domestic animals and thoroughbred horses in addition to humans are desired patients for such treatment with the proteins of the present invention.

The therapeutic method includes administering the composition topically, systematically, or locally as an implant or device. When administered, the therapeutic composition for use in this invention is, of course, in a pyrogen-free, physiologically acceptable form. Further, the composition may desirably be encapsulated or injected in a viscous form for delivery to the site of cartilage and/or bone or tissue damage. Topical administration may be suitable for wound healing and tissue repair. Preferably for bone and/or cartilage formation, the composition includes a matrix capable of delivering the cartilage/bone proteins of the invention to the site of bone and/or cartilage damage, providing a structure for the developing bone and cartilage and optimally capable of being resorbed into the body. Matrices may provide slow release of the cartilage and/or bone inductive proteins proper presentation and appropriate enviroment for cellular infiltration. Matrices may be formed of materials presently in use for other implanted medical applications.

The choice of matrix material is based on biocompatibility, biodegradability, mechanical properties, cosmetic appearance and interface properties. The particular application of the compositions of the invention will define the appropriate formulation. Potential matrices for the compositions are biodegradable and chemically defined calcium sulfate, tricalciumphosphate, hydroxyapatite, polylactic acid and polyanhydrides. Other potential materials are biodegradable and biologically well defined, such as bone or dermal collagen. Further matrices are comprised of pure proteins or extracellular matrix components. Other potential matrices are nonbiodegradable and chemically defined, such as sintered hydroxyapatite, bioglass, aluminates, or other ceramics. Matrices may be comprised of combinations of any of the above mentioned types of material, such as polylactic acid and hydroxyapatite or collagen and tricalciumphosphate. The bioceramics may be altered in composition, such as in calcium-aluminate-phosphate and processing to alter pore size, particle size, particle shape, and biodegradability.

The dosage regimen will be determined by the attending physician considering various factors which modify the action of the proteins of the invention. Factors which may modify the action of the proteins of the invention include the amount of bone weight desired to be formed, the site of bone damage, the condition of the damaged bone, the size of a wound, type of damaged tissue, the patient's age, sex, and diet, the severity of any infection, time of administration and other clinical factors. The dosage may vary with the type of matrix used in the reconstitution and the type or types of bone and/or cartilage proteins present in the composition. The addition of other known growth factors, such as EGF, PDGF, TGF-α, TGF-β, and IGF-I to the final composition, may also effect the dosage.

Progress can be monitored by periodic assessment of cartilage and/or bone growth and/or repair. The progress can be monitored, for example, using x-rays, histomorphometric determinations and tetracycline labeling.

The following examples illustrate practice of the present invention in recovering and characterizing bovine cartilage and/or bone proteins of the invention and employing these proteins to recover the corresponding human protein or proteins and in expressing the proteins via recombinant techniques.

EXAMPLE I

Isolation of Bovine Cartilage/Bone Inductive Protein

Ground bovine bone powder (20–120 mesh, Helitrex) is prepared according to the procedures of M. R. Urist et al., *Proc. Natl Acad. Sci USA*, 70:3511 (1973) with elimination of some extraction steps as identified below. Ten kgs of the ground powder is demineralized in successive changes of 0.6N HCl at 4½° C. over a 48 hour period with vigorous stirring. The resulting suspension is extracted for 16 hours at 4½° C. with 50 liters of 2M $CaCl_2$ and 10 mM ethylenediamine-tetraacetic acid [EDTA], and followed by extraction for 4 hours in 50 liters of 0.5M EDTA. The residue is washed three times with distilled water before its resuspension in 20 liters of 4M guanidine hydrochloride [GuCl], 20 mM Tris (pH 7.4), 1 mM N-ethylmaleimide, 1 mM iodoacetamide, 1 mM phenylmethylsulfonyl fluorine as described in *Clin. Orthop. Rel. Res.*, 171: 213 (1982). After 16 to 20 hours the supernatant is removed and replaced with another 10 liters of GuCl buffer. The residue is extracted for another 24 hours.

The crude GuCl extracts are combined, concentrated approximately 20 times on a Pellicon apparatus with a 10,000 molecular weight cut-off membrane, and then dialyzed in 50 mm Tris, 0.1M NaCl, 6M urea (pH7.2), the starting buffer for the first column. After extensive dialysis the protein is loaded on a 4 liter DEAE cellulose column and the unbound fractions are collected.

The unbound fractions are concentrated and dialyzed against 50 mM NaAc, 50 mM NaCl (pH 4.6) in 6M urea. The unbound fractions are applied to a carboxymethyl cellulose column. Protein not bound to the column is removed by extensive washing with starting buffer, and the material containing protein having bone and/or cartilage formation activity as measured by the Rosen-modified Sampath—Reddi assay (described in Example III below) desorbed from the column by 50 mM NaAc, 0.25 mM NaCl, 6M urea (pH 4.6). The protein from this step elution is concentrated 20- to 40-fold, then diluted 5 times with 80 mM $KPO_4$, 6M urea (pH6.0). The pH of the solution is adjusted to 6.0 with 500 mM $K_2HPO_4$. The sample is applied to an hydroxylapatite column (LKB) equilibrated in 80 mM $KPO_4$, 6M urea (pH6.0) and all unbound protein is removed by washing the column with the same buffer. Protein having bone and/or cartilage formation activity is eluted with 100 mM $KPO_4$ (pH7.4) and 6M urea.

The protein is concentrated approximately 10 times, and solid NaCl added to a final concentration of 0.15M. This material is applied to a heparin—Sepharose column equilibrated in 50 mM $KPO_4$, 150 mM NaCl, 6M urea (pH7.4). After extensive washing of the column with starting buffer, a protein with bone and/or cartilage inductive activity is eluted by 50 mM $KPO_4$, 700 mM NaCl, 6M urea (pH7.4). This fraction is concentrated to a minimum volume, and 0.4 ml aliquots are applied to Superose 6 and Superose 12 columns connected in series, equilibrated with 4M GuCl, 20 mM Tris (pH7.2) and the columns developed at a flow rate of 0.25 ml/min. The protein demonstrating bone and/or cartilage inductive activity corresponds to an approximate 30,000 dalton protein.

The above fractions from the superose columns are pooled, dialyzed against 50 mM NaAc, 6M urea (pH4.6), and applied to a Pharmacia MonoS HR column. The column is developed with a gradient to 1.0M NaCl, 50 mM NaAc, 6M urea (pH4.6). Active bone and/or cartilage formation fractions are pooled. The material is applied to a 0.46×25 cm Vydac C4 column in 0.1% TFA and the column developed with a gradient to 90% acetonitrile, 0.1% TFA (31.5% acetonitrile, 0.1% TFA to 49.5% acetonitrile, 0.1% TFA in 60 minutes at 1 ml per minute). Active material is eluted at approximately 40–44% acetonitrile. Fractions were assayed for cartilage and/or bone formation activity. The active material is further fractionated on a MonoQ column. The protein is dialyzed against 6M urea, 25 mM diethanolamine, pH 8.6 and then applied to a 0.5 by 5 cm MonoQ column (Pharmacia) which is developed with a gradient of 6M urea, 25 mM diethanolamine, pH 8.6 and 0.5M NaCl, 6M urea, 25 mM diethanolamine, pH 8.6. Fractions are brought to pH3.0 with 10% trifluoroacetic acid (TFA).

Aliquots of the appropriate fractions are iodinated by one of the following methods: P. J. McConahey et al, *Int. Arch. Allergy*, 29:185–189 (1966); A. E. Bolton et al, *Biochem J.*, 133:529 (1973); and D. F. Bowen-Pope, *J. Biol. Chem.*, 237:5161 (1982). The iodinated proteins present in these fractions are analyzed by SDS gel electrophoresis.

EXAMPLE II

Characterization of Bovine Cartilage/Bone Inductive Factor

A. Molecular Weight

Approximately 5 µg protein from Example I in 6M urea, 25 mM diethanolamine, pH 8.6, approximately 0.3M NaCl is made 0.1% with respect to SDS and dialyzed against 50 mM tris/HCl 0.1% SDS pH 7.5 for 16 hrs. The dialyzed material is then electrophorectically concentrated against a dialysis membrane [Hunkapillar et al *Meth. Enzymol.* 91: 227–236 (1983)] with a small amount of I 125 labelled counterpart. This material (volume approximately 100 µl) is loaded onto a 12% polyacrylamide gel and subjected to SDS-PAGE [Laemmli, U.K. *Nature*, 227:680–685 (1970)] without reducing the sample with dithiothreitol. The molecular weight is determined relative to prestained molecular weight standards (Bethesda Research Labs). Following autoradiography of the unfixed gel the approximate 28,000–30,000 dalton band is excised and the protein electrophoretically eluted from the gel (Hunkapillar et al supra). Based on similar purified bone fractions as described in the co-pending "BMP" applications described above wherein bone and/or cartilage activity is found in the 28,000–30,000 region, it is inferred that this band comprises bone and/or cartilage inductive fractions.

B. Subunit Characterization

The subunit composition of the isolated bovine bone protein is also determined. The eluted protein described above is fully reduced and alkylated in 2% SDS using iodoacetate and standard procedures and reconcentrated by electrophoretic packing. The fully reduced and alkylated sample is then further submitted to SDS-PAGE on a 12% gel and the resulting approximate 14,000–20,000 dalton region having a doublet appearance located by autoradiography of the unfixed gel. A faint band remains at the 28,000–30,000 region. Thus the 28,000–30,000 dalton protein yields a broad region of 14,000–20,000 which may otherwise also be interpreted and described as comprising two broad bands of approximately 14,000–16,000 and 16,000–20,000 daltons.

EXAMPLE III

Rosen Modified Sampath-Reddi Assay

A modified version of the rat bone formation assay described in Sampath and Reddi, *Proc. Natl. Acad. Sci. U.S.A.*, 80:6591–6595 (1983) is used to evaluate bone and/or cartilage activity of the proteins of the invention. This modified assay is herein called the Rosen-modified Sampath-Reddi assay. The ethanol precipitation step of the Sampath-Reddi procedure is replaced by dialyzing (if the composition is a solution) or diafiltering (if the composition is a suspension) the fraction to be assayed against water. The solution or suspension is then redissolved in 0.1% TFA, and the resulting solution added to 20 mg of rat matrix. A mock rat matrix sample not treated with the protein serves as a control. This material is frozen and lyophilized and the resulting powder enclosed in #5 gelatin capsules. The capsules are implanted subcutaneously in the abdominal thoracic area of 21–49 day old male Long Evans rats. The implants are removed after 5–21 days. Half of each implant is used for alkaline phosphatase analysis [See, A. H. Reddi et al., *Proc. Natl Acad Sci.*, 69:1601 (1972)].

The other half of each implant is fixed and processed for histological analysis. Glycolmethacrylate sections (1 μm) are stained with Von Kossa and acid fuschin or toluidine blue to score the amount of induced bone and cartilage formation present in each implant. The terms +1 through +5 represent the area of each histological section of an implant occupied by new bone and/or cartilage cells and newly formed bone and matrix. Two scoring methods are herein described. The first describes the original scoring method while the second describes the later adopted scoring method. A score of +5 indicates that greater than 50% of the implant is new bone and/or cartilage produced as a direct result of protein in the implant. A score of +4, +3, +2 and +1 would indicate that greater than 40%, 30%, 20% and 10% respectively of the implant contains new cartilage and/or bone. The scoring method later adopted (which herein after maybe referred to as the "modified" scoring method) is as follows: Three non-adjacent sections are evaluated from each implant and averaged. "+/−" indicates tentative identification of cartilage or bone; "+2", >25%; "+3+", >50%; "+4", >75%; "+5", >80%. The scores of the individual implants are tabulated to indicate assay variability.

It is contemplated that the dose response nature of the cartilage and/or bone inductive protein containing samples of the matrix samples will demonstrate that the amount of bone and/or cartilage formed increases with the amount of cartilage/bone inductive protein in the sample. It is contemplated that the control samples will not result in any bone and/or cartilage formation.

As with other cartilage and/or bone inductive proteins such as the above-mentioned "BMP" proteins, the bone and/or cartilage formed is expected to be physically confined to the space occupied by the matrix. Samples are also analyzed by SDS gel electrophoresis and isoelectric focusing followed by autoradiography. The activity is correlated with the protein bands and pI. To estimate the purity of the protein in a particular fraction an extinction coefficient of 1 OD/mg-cm is used as an estimate for protein and the protein is run on SDS PAGE followed by silver staining or radioiodination and autoradiography.

EXAMPLE IV

Bovine BMP-6 Protein Composition

The gel slice of the approximate 14,000–20,000 dalton region described in Example IIB is fixed with methanol-acetic acid-water using standard procedures, briefly rinsed with water, then neutralized with 0.1M ammonium bicarbonate. Following dicing the gel slice with a razor blade, the protein is digested from the gel matrix by adding 0.2 μg of TPCK-treated trypsin (Worthington) and incubating the gel for 16 hr. at 37 degrees centigrade. The resultant digest is then subjected to RPHPLC using a C4 Vydac RPHPLC column and 0.1% TFA-water 0.1% TFA water-acetonitrile gradient. The resultant peptide peaks were monitored by UV absorbance at 214 and 280 nm and subjected to direct amino terminal amino acid sequence analysis using an Applied Biosystems gas phase sequenator (Model 470A). one tryptic fragment is isolated by standard procedures having the following amino acid sequence as represented by the amino acid standard three-letter symbols and where "Xaa" indicates an unknown amino acid the amino acid in parentheses indicates uncertainty in the sequence:

Xaa-His-Glu-Leu-Tyr-Val-Ser-Phe-(Ser)

The following four oligonucleotide probes are designed on the basis of the amino acid sequence of the above-identified tryptic fragment and synthesized on an automated DNA synthesizer.

PROBE #1: GTRCTYGANATRCANTC
PROBE #2: GTRCTYGANATRCANAG
PROBE #3: GTRCTYAAYATRCANTC
PROBE #4: GTRCTYAAYATRCANAG

The standard nucleotide symbols in the above identified probes are as follows: A,adenine; C,cytosine; G,guanine; T,thymine; N, adenosine or cytosine or guanine or thymine, R,adenosine or guanine; and Y,cytosine or thymine.

Each of the probes consists of pools of oligonucleotides. Because the genetic code is degenerate (more than one codon can code for the same amino acid), a mixture of oligonucleotides is synthesized that contains all possible nucleotide sequences encoding the amino acid sequence of the tryptic fragment. These probes are radioactively labeled and employed to screen a bovine cDNA library as described below.

Poly(A) containing RNA is isolated by oligo(dT) cellulose chromatography from total RNA isolated from fetal bovine bone cells by the method of Gehron-Robey et al in *Current Advances in Skeletogenesis*, Elsevier Science Publishers (1985). The total RNA was obtained from Dr. Marian Young, National Institute of Dental Research, National Institutes of Health. A cDNA library is made in lambda gt10 (Toole et al supra) and plated on 50 plates at 8000 recombinants per plate. These recombinants (400,000) are screened on duplicate nitrocellulose filters with a combination of Probes 1, 2, 3, and 4 using the Tetramethylammonium chloride (TMAC) hybridization procedure [see Wozney et al *Science*, 242: 1528–1534 (1988)]. Twenty-eight positives are obtained and are replated for secondaries. Duplicate nitrocellulose replicas again are made. One set of filters are screened with Probes 1 and 2; the other with Probes 3 and 4. Six positives are obtained on the former, 21 positives with the latter. One of the six, called HEL5, is plaque purified, a phage plate stock made, and bacteriophage DNA isolated. This DNA is digested with EcoRI and subcloned into M13 and pSP65. The DNA sequence and derived amino acid sequence of this fragment is shown in Table I.

DNA sequence analysis of this fragment in M13 indicates that it encodes the desired tryptic peptide sequence set forth above, and this derived amino acid sequence is preceded by a basic residue (Lys) as predicted by the specificity of trypsin. The underlined portion of the sequence in FIG. 1 from amino acid #42 to #48 corresponds to the tryptic fragment identified above from which the oligonucleotide probes are designed. The derived amino acid sequence Ser-Gly-Ser-His-Gln-Asp-Ser-Ser-Arg as set forth in FIG. 1 from amino acid #15 to #23 is noted to be similar to a tryptic fragment sequence Ser-Thr-Pro-Ala-Gln-Asp-Val-Ser-Arg found in the 28,000–30,000 dalton purified bone preparation as described in the "BMP" co-pending applications mentioned above. This fragment set forth in FIG. 1 is a portion of the DNA sequence which encodes a bovine BMP-5 protein. The DNA sequence indicates an open reading frame from the 5' end of the clone of 420 base pairs, encoding a partial peptide of 140 amino acid residues (the first 7 nucleotides are of the adaptors used in the cloning procedure). An in-frame stop codon (TAA) indicates that this clone encodes the carboxy-terminal part of a bovine BMP-5 cartilage/bone protein.

The remaining positive clones isolated with probes #1, #2, #3, and #4 described above are screened with HEL5 and a further clone is identified under reduced stringency conditions [5× SSC, 0.1% SDS, 5× Denhardt's, 100 µg/ml salmon sperm DNA standard hybridization buffer (SHB) at 65° C., wash in 2× SSC 0.1% SDS at 65° C.]. This clone is plaque purified, a phage plate stock made and bacteriophage DNA isolated. The DNA sequence and derived amino acid sequence of a portion of this clone is shown in FIG. 2. This sequence represents the DNA sequence encoding a BMP-6 cartilage/bone protein of the invention.

The first underlined portion of the sequence in FIG. 2 from amino acid #97–amino acid #105 Ser-Thr-Pro-Ala-Gln-Asp-Val-Ser-Arg corresponds to the tryptic fragment found in the 28,000–30,000 dalton purified bovine bone preparation (and its reduced form at approximately 18,000–20,000 dalton reduced form) as described in the "BMP" co-pending applications mentioned above. The second underlined sequence in FIG. 2 from amino acid #124–amino acid #130 corresponds to the tryptic fragment identified above from which the oligonucleotide probes are designed.

The DNA sequence of FIG. 2 indicates an open reading frame of 666 base pairs starting from the 5' end of the sequence of FIG. 2, encoding a partial peptide of 222 amino acid residues. An in-frame stop codon (TGA) indicates that this clone encodes the carboxy-terminal part of a bovine BMP-6 protein of the invention. Based on knowledge of other BMP proteins and other proteins in the TGF-β family, it is predicted that the precursor polypeptide would be cleaved at the three basic residues (ArgArgArg) to yield a mature peptide beginning with residue 90 or 91 of the sequence of FIG. 2.

EXAMPLE V

Human BMP-6 Proteins

Human cell lines which synthesize BMP-5 and/or BMP-6 mRNAs are identified in the following manner. RNA is isolated from a variety of human cell lines, selected for poly(A)-containing RNA by chromatography on oligo(dT) cellulose, electrophoresed on a formaldehyde-agarose gel, and transferred to nitrocellulose. A nitrocellulose replica of the gel is hybridized to a single standed M13 $^{32}$P-labeled probe corresponding to the above mentioned BMP-5 EcoRI-BglII fragment containing nucleotides 1–465 of the sequence of Table I. A strongly hybridizing band is detected in the lane corresponding to the human osteosarcoma cell line U-20S RNA. Another nitrocellulose replica is hybridized to a single stranded M13 $^{32}$P-labeled probe containing the PstI-SmaI fragment of bovine BMP-6 (corresponding to nucleotides 106–261 of FIG. 2. It is found that several RNA species in the lane corresponding to U-20S RNA hybridize to this probe.

A cDNA Library is made in the vector lambda ZAP (Stratagene) from U-20S poly(A)-containing RNA using established techniques (Toole et al.). 750,000 recombinants of this library are plated and duplicate nitrocellulose replicas made. The SmaI fragment of bovine BMP-6 corresponding to nucleotides 259–751 of FIG. 2 is labeled by nick-translation and hybridized to both sets of filters in SHB at 65°. One set of filters is washed under stringent conditions (0.2× SSC, 0.1% SDS at 65°), the other under reduced stringency conditions (1× SSC, 0.1% SDS at 65°). Many duplicate hybridizing recombinants (approximately 162) are noted. 24 are picked and replated for secondaries. Three nitrocellulose replicas are made of each plate. One is hybridized to the BMP-6 SmaI probe, one to a nick-translated BMP-6 PstI-SacI fragment (nucleotides 106–378 of FIG. 2), and the third to the nick-translated BMP-5 XbaI fragment (nucleotides 1–76 of FIG. 1). Hybridization and washes are carried out under stringent conditions.

Six clones which hybridize to the second probe more strongly than to the third are picked and transformed into plasmids. Restriction mapping, Southern blot analysis, and DNA sequence analysis of these plasmids indicate that there are two classes of clones. Clones U2-7 and U2-10 contain human BMP-6 coding sequence based on their stronger hybridization to the second probe and closer DNA homology to the bovine BMP-6 sequence of FIG. 2 than the other 4 clones. DNA sequence data derived from these clones indicates that they encode a partial polypeptide of 132 amino acids comprising the carboxy-terminus of the human BMP-6 protein. U2-7 was deposited with the American Type Culture Collection (ATCC), 10801 University Boulevard, Manassas, Va. on Jun. 23, 1989 under accession number 68021.

A primer extended cDNA library is made from U-2 OS mRNA using the oligonucleotide GGAATCCAAGGCAGAATGTG, the sequence being based on the 3' untranslated sequence of the human BMP-6 derived from the clone U2-10. This library is screened with an oligonucleotide of the sequence CAGAGTCGTAATCGC, derived from the BMP-6 coding sequence of U2-7 and U2-10. Hybridization is in standard hybridization buffer (SHB) at 42 degrees centigrade, with wash conditions of 42 degrees centigrade, 5× SSC, 0.1% SDS. Positively hybridizing clones are isolated. The DNA insert of one of these clones, PEH6-2 indicates that it extends further in a 5' direction than either U2-7 or U2-10. A primer extended cDNA library constructed from U-20S mRNA as above is screened with an oligonucleotide of the sequence GCCTCTCCCCCTCCGACGCCCCGTCCT-CGT, derived from the sequence near the 5' end of PEH6-2. Hybridization is at 65 degrees centigrade in SHB, with washing at 65 degrees centigrade in 2× SSC, 0.1% SDS. Positively hybridizing recombinants are isolated and analyzed by restriction mapping and DNA sequence analysis.

The 5' sequence of the insert of one of the positively hybridizing recombinants, PE5834#7, is used to design an oligonucleotide of the sequence CTGCTGCTCCTCCT-GCTGCCGGAGCGC. A random primed cDNA library [synthesized as for an oligo (dT) primed library except that $(dN)_6$ is used as the primer] is screened with this oligonucleotide by hybridization at 65 degrees centigrade in SHB with washing at 65 degrees centigrade in 1× SSC, 0.1% SDS. A positively hybridizing clone, RP10, is identified, isolated, and the DNA sequence sequence from the 5' end of its insert is determined. This sequence is used to design an oligonucletide of the sequence TCGGGCTTCCTGTACCG-GCGGCTCAAGACGCAGGAGAAGCGGGAGATGCA. A human placenta cDNA library (Stratagene catalog #936203) is screened with this oligonucleotide by hybridization in SHB at 65 degrees centigrade, and washing at 65 degrees centigrade with 0.2× SSC, 0.1% SDS. A positively hybridizing recombinant designated BMP6C35 is isolated. DNA sequence analysis of the insert of this recombinant indicates that it encodes the complete human BMP-6 protein. BMP6C35 was deposited with the American Type Culture Collection, 10801 University Boulevard, Manassas, Va. USA on Mar. 1, 1990 under Accession Number 68245.

The DNA and derived amino acid sequence of the majority of the insert of BMP6C35 is given in FIG. 3. This DNA sequence contains an open reading frame of 1539 base pairs which encodes the 513 amino acid human BMP-6 protein precursor. The presumed initiator methionine codon is preceded by a 5'untranslated sequence of 159 base pairs with stop codons in all three reading frames. The stop codon at nucleotides 1699–1701 is followed by at least 1222 base pairs of 3'untranslated sequence. It is noted that U2-7 has a C residue at the position corresponding to the T residue at position 1221 of BMP6C35; U2-7 also has a C residue at the position corresponding to the G residue at position 1253 of BMP6C35. These do not cause amino acid differences in the encoded proteins, and presumably represent allelic variations.

The oligonucleotide TCGGGCTTCCTGTACCGGCG-GCTCAAGACGCAGGAGAAGCGGGAGATGCA is used to screen a human genomic library (Toole et al supra), by hybridizing nitrocellulose replicas of $1 \times 10^6$ recombinants with the oligonucleotide in SHB at 65 degrees centigrade, and washing at 65 degrees centigrade with 0.2× SSC, 0.1% SDS. Positively hybridizing clones are purified. The oligonucleotide hybridizing region is localized to an approximately 1.5 kb Pst I fragment. DNA sequence analysis of this fragment confirms the 5' sequence indicated in FIG. 3.

The DNA sequence of the human BMP-6 clone set forth in FIG. 3 reveals an open reading frame of 1539 bp encoding a protein of 513 amino acids. The first underlined portion of the sequence in FIG. 3 from amino acid #388 to #396,Ser-Thr-Gln-Ser-Gln-Asp-Val-Ala-Arg, corresponds to the similar sequence Ser-Thr-Pro-Ala-Gln-Asp-Val-Ser-Arg of the bovine sequence described above and set forth in FIG. 2. The second underlined sequence in FIG. 3 from amino acid #415 through #421 His-Glu-Leu-Tyr-Val-Ser-Phe, corresponds to the tryptic fragment identified above from which the oligonucleotide probes are designed. When the tryptic sequence His-Glu-Leu-Tyr-Val-Ser-Phe-(Ser) described above was identified, it was noted to be similar to a sequence found in other BMP proteins for example the sequence His-Pro-Leu-Tyr-Val-Asp-Phe-Ser found in the bovine and human cartilage/bone protein BMP-2A sequence as described in co-pending U.S. application Ser. No. 179,100, U.S. Pat. No. 5,013,649. BMP-6 therefore represents a new member of the BMP subfamily of TGF-β like molecules which includes the molecules BMP-2 (also sometimes referred to as BMP-2A or BMP-2 Class I), 3, 4 (also sometimes referred to as BMP-2B or BMP-2 Class II), 5 and 7 described in co-pending applications cited above.

Based on knowledge of other BMP proteins, as well as other proteins in the TGF-β family, BMP-6 is predicted to be synthesized as a precursor molecule and the precursor polypeptide would be cleaved between amino acid #381 and amino acid #382 yielding a 132 amino acid mature polypeptide with a calculated molecular weight of approximately 15 Kd. The mature form of BMP-6 contains three potential N-linked glycosylation sites per polypeptide chain.

It is contemplated that the active BMP-6 protein molecule is a dimer. It is further contemplated tht the processing of BMP-6 into the mature form involves dimerization and removal of the N-terminal region in a manner analogous to the processing of the related protein TGF-β [L. E. Gentry, et al., *Molec. & Cell. Biol.* 8:4162 (1988); R. Dernyck, et al., *Nature* 316:701 (1985)].

Comparision of the sequence of murine Vgr-1 [Lyons, et al., *PNAS* 86:4554 (1989)] to human BMP-6 reveals a degree of amino acid sequence identity greater than 92% The murine Vgr-1is likely the murine homologue of BMP-6. Human BMP-6 shares homology with other BMP molecules as well as other members of the TGF-β superfamily of molecules. The cysteine-rich carboxy-terminal 102 amino acid residues of human BMP-6 shares the following homologies with BMP proteins disclosed in copending applications described above: 61% identity with BMP-2; 44% identity with BMP-3, 60% identity with BMP-4; 91% identity with BMP-5; and 87% identity with BMP-7. Human BMP-6 further shares the following homologies: 41% identity with TGF-β3; 39% identity with TGF-β2; 37% identity with TGF-β1; 26% identity with Mullerian Inhibiting Substance (MIS), a testicular glycoprotein that causes regression of the Mullerian duct during development of the male embryo; 25% identity with inhibin α; 43% identity with inhibin $β_B$; 49% identity with inhibin $β_A$; 58% identity with Vg1, a Xenopus factor which may be involved in mesoderm induction in early embryogenesis [Weeks and Melton, *Cell* 51:861–867(1987)]; and 59% identity with Dpp the product of the Drosophila decapentaplegic locus which is required for dorsal-ventral specification in early embryogenesis and is involved in various other developmental processes at later stages of development [Padgett, et al., *Nature* 325:81–84 (1987)].

The procedures described above and additional methods known to those skilled in the art may be employed to isolate other related proteins of interest by utilizing the bovine or human proteins as a probe source. Such other proteins may find similar utility in, inter alia, fracture repair, wound healing and tissue repair.

Additional methods known to those skilled in the art may be used to isolate the genetic material encoding human and other species' cartilage/bone proteins of the invention.

EXAMPLE VI

Expression of the BMP-6 Proteins

In order to produce bovine, human or other mammalian proteins of the invention, the DNA encoding it is transferred into an appropriate expression vector and introduced into mammalian cells or other preferred eukaryotic or prokaryotic hosts by conventional genetic engineering techniques. It is contemplated that the preferred expression system for biologically active recombinant human proteins of the invention will be stably transformed mammalian cells. It is further contemplated that the preferred mammalian cells will be CHO cells. The transformed host cell is cultured and the BMP-6 proteins expressed thereby are recovered and purified. The recombinantly expressed BMP-6 proteins are free of proteinaceous materials with which they ordinarily are associated in nature and are purified from other proteinaceous materials with which they are co-produced as well as from other contaminants, such as materials found in the culture media.

In order to express biologically active human BMP-6 proteins, a selected host cell is transformed, using techniques known to those skilled in the art of genetic engineering, with a DNA sequence encoding human BMP-6 protein. The DNA encoding BMP-6 comprises nucleotide #1393 to #1698 set forth in FIG. 3 encoding amino acid #412 to #513. The transformed host cells are cultured and the BMP-6 protein comprising amino acid #412 to amino acid #513 as set forth in FIG. 3 is expressed. The expressed protein is recovered, isolated and purified form the culture and culture medium. The purified protein is substantally free from other proteinaceous materials with which it is co-produced as well as from other contaminants. In other embodiments, the DNA sequence utilized in expressing human BMP-6 proteins of the invention comprise the longer nucleotide sequence comprising nucleotide #1321 to #1698 encoding the amino acid sequence comprising #388 to #513. In further embodiment the DNA sequence utilized in expression comprises nucleotide #1303 to #1698 encoding the amino acid sequence comprising amino acid #382 to #513.

Expression in CHO cells for instance any comprise transformation of the host cell with a vector containing a DNA sequence comprising nucleotides #160 through #1712 of FIG. 3. The transformed host cell is cultured and the expressed BMP-6 proteins are recovered and purified. It is contemplated that the recovered and purified BMP-6 protein comprises what is expected to be the mature form comprising amino acid #382–513. However, other forms of BMP-6 may be recovered and purified. These forms include proteins comprising amino acid #388–#513 and proteins comprising amino acid #412 to #513 as set forth in FIG. 3.

One skilled in the art can construct mammalian expression vectors by employing the DNA sequences of the invention sequences and known vectors, such as pCD [Okayama et al., *Mol. Cell Biol.*, 2:161–170 (1982)] and pJL3, pJL4 [Gough et al., *EMBO J.*, 4:645–653 (1985)]. The transformation of these vectors into appropriate host cells may result in expression of the proteins of the invention.

One skilled in the art could manipulate the sequences of the invention by eliminating or replacing the mammalian regulatory sequences flanking the coding sequence with bacterial sequences to create bacterial vectors for intracellular or extracellular expression by bacterial cells. The coding sequences could be further manipulated, for example, ligated to other known linkers or modified by deleting non-coding sequences there-from or altering nucleotides therein by other known techniques. The modified coding sequence could then be inserted into a known bacterial vector using procedures such as described in T. Taniguchi et al., *Proc. Natl Acad. Sci. USA*, 77:5230–5233 (1980). This exemplary bacterial vector could then be transformed into bacterial host cells and a protein of the invention expressed thereby. For a strategy for producing extracellular expression of a cartilage and/or bone protein of the invention in bacterial cells., see, e.g. European patent application EPA 177,343.

Similar manipulations can be performed for the construction of an insect vector [See, e.g. procedures described in published European patent application 155,476] for expression in insect cells. A yeast vector could also be constructed employing yeast regulatory sequences for intracellular or extracellular expression of the factors of the present invention by yeast cells. [See, e.g., procedures described in published PCT application WO86/00639 and European patent application EPA 123,289].

A method for producing high levels of a protein of the invention from mammalian cells involves the construction of cells containing multiple copies of the heterologous gene encoding proteins of the invention. The heterologous gene may be linked to an amplifiable marker, e.g. the dihydrofolate reductase (DHFR) gene for which cells containing increased gene copies can be selected for propagation in increasing concentrations of methotrexate (MTX) according to the procedures of Kaufman and Sharp, *J. Mol. Biol.*, 159:601–629 (1982). This approach can be employed with a number of different cell types.

For example, a plasmid containing a DNA sequence for a protein of the invention in operative association with other plasmid sequences enabling expression thereof and the DHFR expression plasmid pAdA26SV(A)3 [Kaufman and Sharp, *Mol. Cell. Biol.*, 2:1304 (1982)] may be co-introduced into DHFR-deficient CHO cells, DUKX-BII, by calcium phosphate coprecipitation and transfection, electroperation or protoplast fusion. DHFR expressing transformants are selected for growth in alpha media with dialyzed fetal calf serum, and subsequently selected for amplification by growth in increasing concentrations of MTX (sequential steps in 0.02, 0.2, 1.0 and 5 uM MTX) as described in Kaufman et al., *Mol Cell Biol.*, 5:1750 (1983). Protein expression should increase with increasing levels of MTX resistance.

Transformants are cloned, and the proteins of the invention are recovered, isolated, and purified from the culture medium. Biologically active protein expression is monitored by the Rosen-modified Sampath-Reddi rat bone formation assay described above in Example III. Similar procedures can be followed to produce other related proteins.

EXAMPLE VII

Biological Activity of Expressed BMP-6 Proteins

To measure the biological activity of the expressed proteins obtained in Example VI above, the BMP-6 proteins are recovered from the culture media and purified. BMP-6 may be partially purified on a Heparin Sepharose column. 4 ml of the collected post transfection conditioned medium supernatant from one 100 mm culture dish is concentrated approximately 10 fold by ultrafiltration on a YM 10 membrane and then dialyzed against 20 mM Tris, 0.15M NaCl, pH 7.4 (starting buffer). This material is then applied to a 1.1 ml Heparin Sepharose column in starting buffer. Unbound proteins are removed by an 8 ml wash of starting buffer, and bound proteins, including proteins of the invention, are desorbed by a 3–4 ml wash of 20 mM Tris, 2.0M NaCl, pH 7.4.

The proteins bound by the Heparin column are concentrated approximately 10-fold on a Centricon 10 and the salt reduced by diafiltration with 0.1% trifluoroacetic acid. The appropriate amount of this solution is mixed with 20 mg of rat matrix and then assayed for in vivo bone and/or cartilage formation activity by the Rosen-modified Sampath-Reddi assay. A mock transfection supernatant fractionation is used as a control.

The implants containing rat matrix to which specific amounts of human BMP-6 proteins of the invention have been added are removed from rats after seven days and processed for histological evaluation. Representative sections from each implant are stained for the presence of new bone mineral with von Kossa and acid fuschin, and for the presence of cartilage-specific matrix formation using toluidine blue. The types of cells present within the section, as well as the extent to which these cells display phenotype are evaluated and scored as described in Example III.

Levels of activity may also be tested for host cell extracts. Partial purification is accomplished in a similar manner as described above except that 6M urea is included in all the buffers.

The foregoing descriptions detail presently preferred embodiments of the present invention. Numerous modifications and variations in practice thereof are expected to occur to those skilled in the art upon consideration of these descriptions. Those modifications and variations are believed to be encompassed within the claims appended hereto.

What is claimed is:

1. A purified human bone morphogenetic protein-6 produced by the steps of
   (a) culturing in a suitable culture medium a cell transformed with a DNA sequence comprising the DNA sequence of FIG. 3 from nucleotide 1321 to 1698; and
   (b) recovering from said culture medium a protein comprising the amino acid sequence from amino acid 388 to amino acid 513 as shown in FIG. 3.

2. A composition comprising a purified [BMP-6] bone morphogenetic protein-6 produced by the steps of
   (a) transforming a host cell with a DNA sequence comprising nucleotides #160 to #1712 of FIG. 3;
   (b) culturing said transformed cell in a suitable culture medium; and
   (c) isolating and purifying said protein from said culture medium.

3. The composition of claim 2 wherein said protein comprises amino acids #382 to #513 of FIG. 3.

4. The composition of claim 2 wherein said protein is characterized by the ability to induce the formation of cartilage and/or bone.

5. A purified bone morphogenetic protein-6 (BMP-6) comprising an amino acid sequence selected from the group consisting of:
   (a) amino acids 412 through 513 of FIG. 3;
   (b) amino acids 388 through 513 of FIG. 3; and
   (c) amino acids 382 through 513 of FIG. 3.

6. The protein of claim 5 wherein said protein is a disulfide linked dimer wherein at least one of the subunits of said dimer comprises amino acids 382 through 513 of FIG. 3.

7. The protein of claim 5 wherein said protein is a disulfide linked dimer wherein at least one of the subunits of said dimer comprises amino acids 388 through 513 of FIG. 3.

8. The protein of claim 5 wherein said protein is a disulfide linked dimer wherein at least one of the subunits of said dimer comprises amino acids 412 through 513 of FIG. 3.

9. A pharnaceutical composition comprising an amount of the BMP-6 protein of claim 5 effective to induce the formation of cartilage and/or bone in admixture with a pharmaceutically acceptable vehicle.

10. A method for inducing bone and/or cartilage formation in a patient in need of same comprising administering to said patient the pharmaceutical composition of claim 9.

11. A BMP-6 protein encoded by a DNA sequence comprising a DNA sequence selected from the group consisting of the DNA molecules of ATCC deposits 68245 and 68021.

12. A BMP-6 protein comprising amino acids 382 through 513 of FIG. 3.

13. A purified BMP-6 polypeptide comprising an amino acid sequence encoded by a DNA sequence comprising a DNA sequence selected from the group consisting of:
   (a) nucleotides 1393 through 1698 of FIG. 3;
   (b) nucleotides 1321 through 1698 of FIG. 3;
   (c) nucleotides 1303 through 1698 of FIG. 3; and
   (d) naturally occurring allelic sequences and degenerative codon sequences of (a) through (c).

14. A purified BMP-6 polypeptide encoded by a DNA sequence which hybridizes under stringent wash conditions of 0.1× SSC at 65° C. to a DNA sequence selected from the group consisting of:
   (a) nucleotides 1393 through 1698 of FIG. 3;
   (b) nucleotides 1321 through 1698 of FIG. 3;
   (c) nucleotides 1303 through 1698 of FIG. 3; and
   (d) naturally occurring allelic sequences and degenerative codon sequences of (a) through (c).

15. A purified BMP-6 polypeptide comprising an amino acid sequence selected from the group consisting of amino acid sequences encoded by a DNA sequence comprising nucleotides 289 through 666 of FIG. 2.

* * * * *